(12) United States Patent
Nottingham et al.

(10) Patent No.: US 6,558,640 B1
(45) Date of Patent: May 6, 2003

(54) HOUSEHOLD PRODUCT SANITIZER (75) Inventors: John R. Nottingham, Hunting Valley, OH (US); Christopher Riker, Lakewood, OH (US); John W. Spirk, Gates Mills, OH (US); Marc L. Vitantonio, South Russell, OH (US)

(73) Assignee: Novalabs, LLC, Cleveland, OH (US)

( * ) Notice: Subject to any disclaimer, the term of this patent is extended or adjusted under 35 U.S.C. 154(b) by 0 days.

(21) Appl. No.: 09/641,307

(22) Filed: Aug. 18, 2000

(51) Int. Cl.[7] .............................. A62B 7/08; A21B 1/00; F26B 11/18; F26B 19/00
(52) U.S. Cl. ...................... 422/307; 422/125; 422/109; 422/55; 422/116; 422/119; 219/400; 34/192; 34/195; 34/202; 34/218; 34/231; 34/233
(58) Field of Search .............................. 422/1–3, 5, 22, 422/28–37, 55, 83, 105, 109, 116, 119, 120, 125, 244, 291–292, 300, 302, 307; 34/192, 195, 197, 202, 218, 231, 233; 219/400

(56) References Cited

U.S. PATENT DOCUMENTS

| | | | |
|---|---|---|---|
| 2,065,895 A | 12/1936 | Jandat .......................... 21/18 |
| 3,820,251 A | * 6/1974 | Abernathy .................... 34/60 |
| 4,080,167 A | 3/1978 | Beers ........................... 21/86 |
| 4,088,445 A | 5/1978 | Ellis et al. .................... 21/83 |
| 4,165,359 A | 8/1979 | Thomas et al. ............. 422/105 |
| 4,256,952 A | 3/1981 | Thomas et al. ............. 219/521 |
| 4,307,288 A | 12/1981 | Stine .......................... 219/521 |
| 4,331,859 A | 5/1982 | Thomas et al. ............. 219/521 |
| 4,388,521 A | 6/1983 | Thomas et al. ............. 219/521 |
| 4,472,623 A | 9/1984 | Futter ........................ 219/521 |
| 4,625,119 A | 11/1986 | Murdock, III ........... 250/455.1 |
| 4,740,706 A | 4/1988 | Murdock, III ........... 250/455.1 |
| 4,788,775 A | * 12/1988 | Ahmed .......................... 34/48 |
| 4,816,648 A | 3/1989 | Dusbabek ................... 219/521 |
| 4,845,859 A | * 7/1989 | Evans ......................... 34/107 |
| 4,869,872 A | * 9/1989 | Baltes ........................... 422/1 |
| 4,894,207 A | 1/1990 | Archer et al. ............... 422/292 |
| 5,164,161 A | 11/1992 | Feathers et al. ............ 422/109 |
| 5,282,264 A | 1/1994 | Reeves et al. .............. 392/382 |
| 5,303,325 A | 4/1994 | Pasternak et al. .......... 392/379 |
| 5,343,632 A | * 9/1994 | Dinh ........................... 34/507 |

* cited by examiner

Primary Examiner—Robert J. Warden, Sr.
Assistant Examiner—Monzer R. Chorbaji
(74) Attorney, Agent, or Firm—Calfee, Halter & Griswold, LLP (57) ABSTRACT

A sanitizer which utilizes hot air to destroy bacteria upon household products such as nursery, bathroom and kitchen items. The sanitizer includes a base, heating element, fan, and a sanitizing chamber with spacers which allow optimal placement of the products being sanitized. The sanitizer includes a vented cover which allows operation within a set temperature range and fast cool down when the sanitizing process is complete.

16 Claims, 9 Drawing Sheets

HOUSEHOLD PRODUCT SANITIZER

FIELD OF THE INVENTION

This invention generally relates to sanitizing devices and more specifically to hot air sanitizers used to disinfect household products, specifically nursery, bathroom and kitchen products.

BACKGROUND OF THE INVENTION

A current trend in the fight against transmittal of germs is the use of anti-bacterial products. For example, many hand soaps have added anti-bacterial ingredients. Sterilization devices have been developed to sanitize objects that may have bacteria upon their surface. Minimizing the presence of bacteria is particularly important in the case of infants because they are more susceptible to infection. Infants also have a tendency to place toys and other objects, potentially contaminated with undesirable bacteria, within their mouths. Typical undesirable bacteria include: Streptococcus Group B, Streptococcus Group A, Hemopholis Influenza, Streptococcus Pneumonia, and Pseudomonas Aeruginosa.

Typical sterilization devices are described in U.S. Pat. No. 4,544,529 (Bottle Sterilizer) to Hoeck, U.S. Pat. No. 4,894,207 (Recirculating High Velocity Hot Air Sterilizing Device) to Archer et. al., and U.S. Pat. No. 4,740,706 (Sanitizer for Bathroom Articles) to Murdock, III. These devices are not desirable for use on all household items. The Hoeck '529 patent describes a sterilizer which utilizes steam to destroy pathogenic microorganisms. This type of sterilizer would not be effective in disinfecting plush toys. Steam would dampen the plush toys.

The Archer '207 patent utilizes hot air to disinfect dental and surgical metal instruments. Preferably air having a temperature in a range from 350 degrees Fahrenheit to 400 degrees Fahrenheit is used. However, it is not desirable to use such hot air in a household device. If the disinfection process is terminated before completion, the operator could be harmed by making contact with very hot items.

The Murdock III patent utilizes a germicidal lamp to sanitize a bathroom article, such as a toothbrush. Articles are hung from spring clips in order to be exposed to the ultraviolet light from the germicidal lamp. However, unlike hot air which may penetrate into and between articles which are placed in close contact with each other, light requires the bathroom articles to be arranged apart from each other to avoid shadowing. Fewer articles can be sanitized utilizing this process and more time must be spend arranging these articles.

A safe, simple, inexpensive, and effective method to destroy bacteria upon household products is desired. Further, an inexpensive device which utilizes this method and can be safely used in the home is desired.

SUMMARY OF THE INVENTION

The present invention overcomes these and other disadvantages of the prior art by providing an improved sanitizing device. The invention provides in one aspect, a sanitizing device for household products, such as nursery, bathroom or kitchen products, including a heating element, a vented sanitizing chamber including integrally formed, protruding spacers, and a fan which moves air across the heating element and into the sanitizing chamber.

The invention provides in another aspect a method used for sanitizing household products including placing the products within a sanitizing chamber, contacting the products with air which has been heated to a desired temperature.

The invention provides a simple way to sanitize both plastic and plush household products. A principle advantage of the invention is that the products, because of a superior spacer system, do not need to be specially arranged to guarantee full sanitization. A novel ventilation system keeps the products from overheating and allows the products to cool down quickly after being sanitized. Thus, the products may be removed quickly from the device and used again in the household.

These and other aspects of the invention are herein described in particularized detail with reference to the accompanying Figures.

DETAILED DESCRIPTION OF PREFERRED AND ALTERNATE EMBODIMENTS

Figure 1:
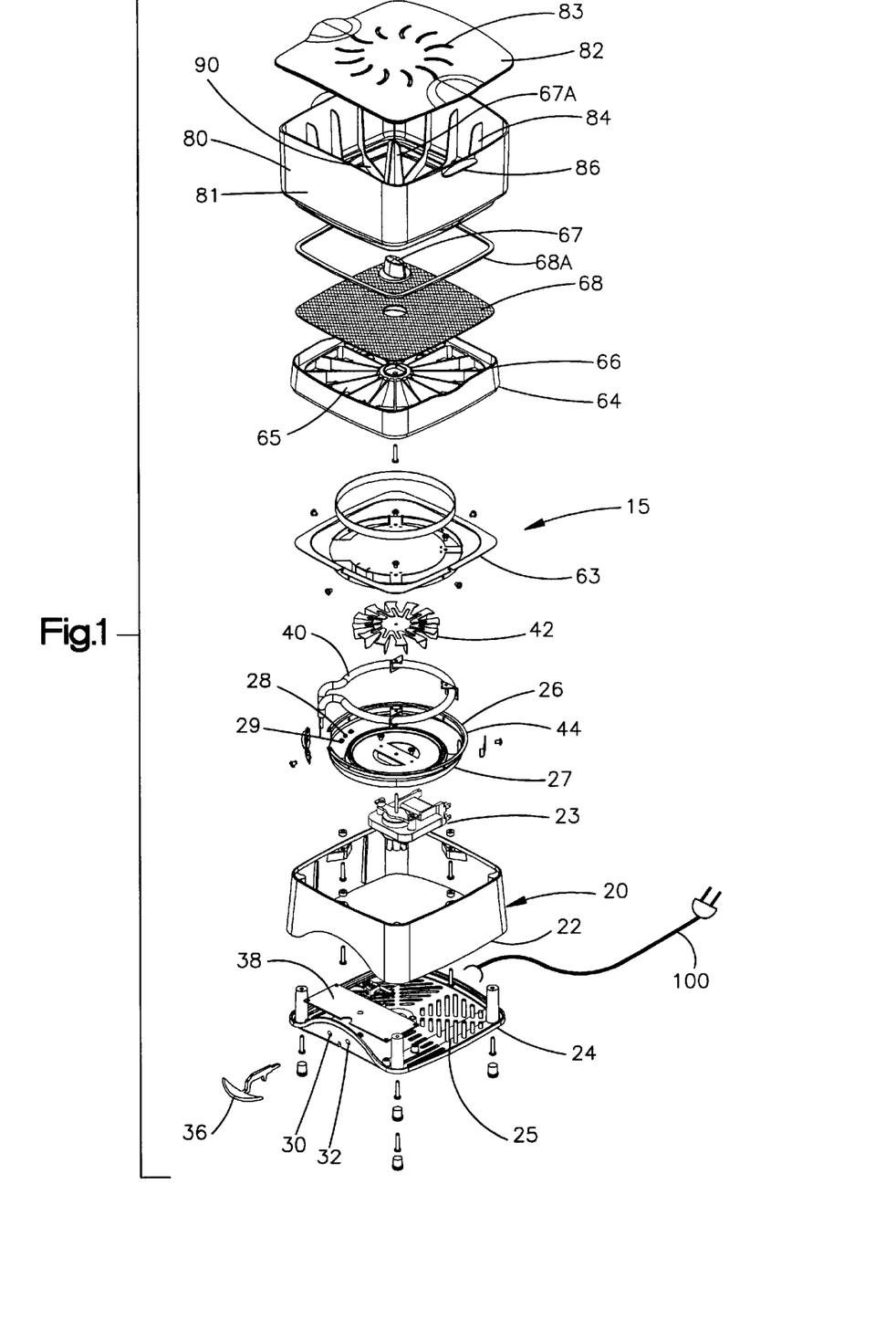
FIG. 1 is an exploded view of the sanitizer including a detailed portion showing a drain hole.

Referring to the drawings, FIG. 1 illustrates a preferred sanitizing device 15 according to the invention. The sanitizing device 15 may be used to sanitize products used in the nursery, kitchen, or bathroom including plastic toys, cloth toys, rattles, and pacifiers. As described in more detail below, the sanitizing device 15 comprises a base 20, a sanitizing chamber 80, a heating element 40, a fan 42, a cover 82 and one or more electronic circuits 38. The invention also comprises a method for sanitizing household products. The method includes placing products within the sanitizing device 15 and the operation of the sanitizing device 15. The operation of the sanitizing device 15 includes: a preheat cycle, a sanitizing cycle, and a cooling cycle.

The sanitizing device 15 utilizes a hot air flow, to sanitize the household products. Ambient air is heated by a heating element 40. Certain types of bacteria may be destroyed by exposure to heat for a predetermined amount of time. Some types of bacteria which may be destroyed are streptococcus groups A and B, hempholis influenza, and streptococcus pneumonia. An effective way to transfer heat to such bacteria is to envelop the bacteria (or the object contaminated by the bacteria) with heated air. The hot air is pushed by a fan 42 into a sanitizing chamber 80 which holds the household products.

Figure 3:
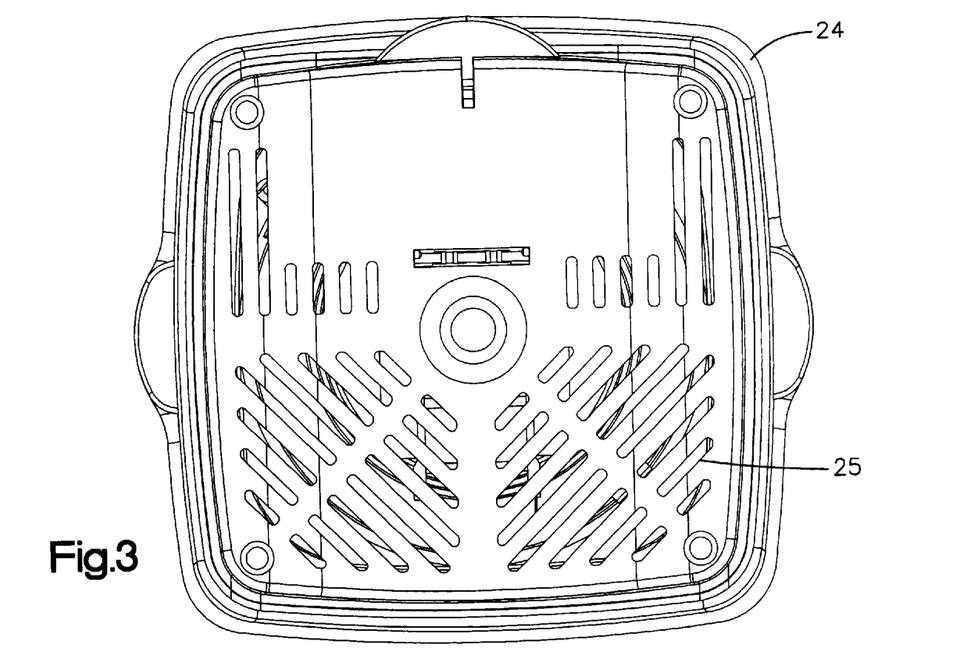
FIG. 3 is a bottom view of the sanitizer.
Figure 4:
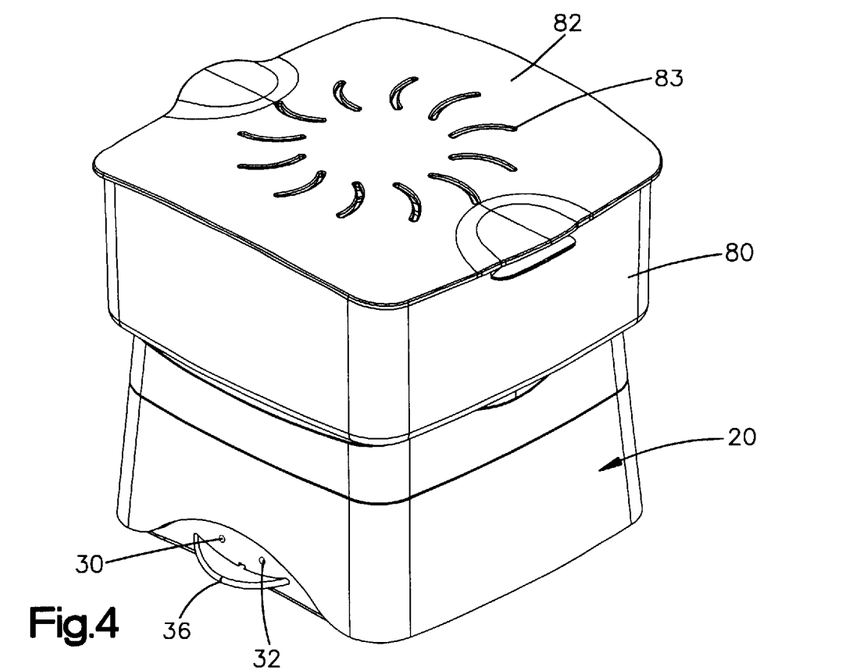
FIG. 4 is a perspective view of the sanitizer.
Figure 5:
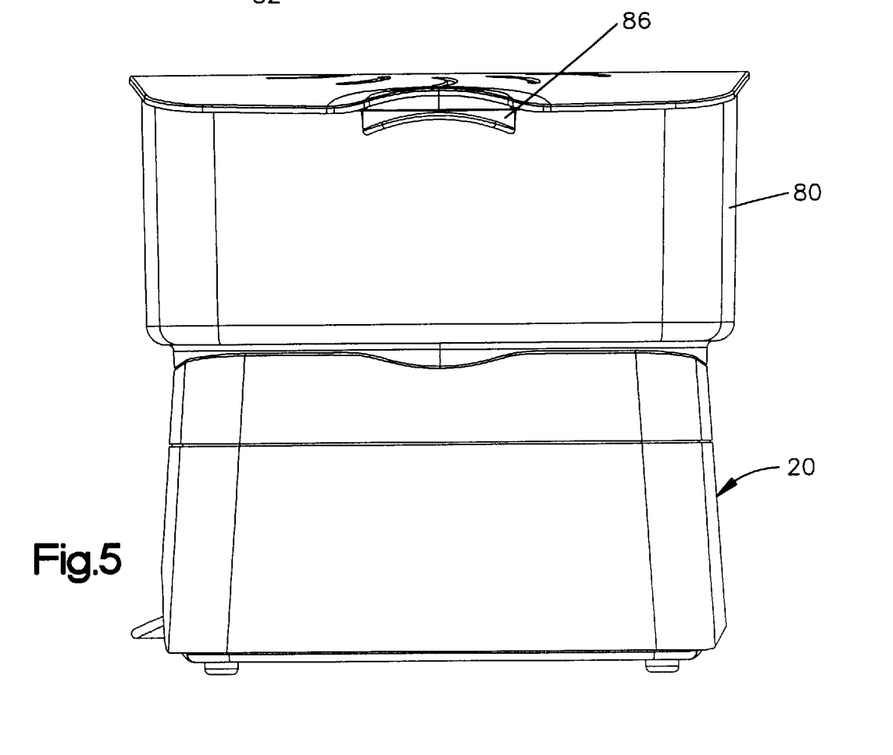
FIG. 5 is a side view of the sanitizer.

The sanitizing device 15 includes a base 20. As described in more detail below, the base 20 includes or supports a motor 23, a heating element 40, a plenum 26, a fan 42 and a switch 36. The base 20 has a lower housing 22 and a bottom plate 24. The lower housing 22 encloses the motor 22, heating element 40, plenum 26 and fan 42. As shown in FIGS. 1 and 3, the bottom plate 24 has one or more vents 25 through which ambient air may be drawn into the sanitizing device 15. The bottom plate 24 is attached to the lower housing 22 using screws although any method of attachment may be substituted. Both the lower housing 22 and the bottom plate 24 are manufactured from a high temperature thermoplastic material.

The base 20 supports a heating element 40. The heating element 40 may be a variety of shapes, however one embodiment includes a tubular shaped heating element 40 formed into a ring. In another embodiment the heating element 40 is rated for 750 watts at 115 volts AC and has a resistance of 17.6 ohms. The motor 23 is powered electrically and is used to rotate the fan 42. In one embodiment the motor 23 is rated at a speed of 3100 RPM while drawing 20 watts of power. The motor 23 includes a shaft upon which a fan 42 is attached. The fan 42 is used to move ambient air across the heating element 40 and into the sanitizing chamber 80. In one embodiment, the fan 42 is a centrifugal impeller type rated to yield 9 to 11 CFM of air at a fan speed of 3100 RPM, although other fan types may be used.

The plenum 26 is located beneath the fan 42, the sanitizing chamber 80, and the heater element 40. The plenum 26 is made in the shape of a bowl and serves three purposes: restricting flow of the heated air in a downward direction, blocking radiant heat generated by the heating element 40, and catching drained liquid. Liquid, which often remains on the products after they have been rinsed and placed in the sanitizing device 15, drains from the products and travels to the plenum base 27. The plenum base 27 is sloped towards a drain hole 28 shown in the detailed portion of FIG. 1. The drain hole 28 is surrounded by a boss 29 which allows drainage from the plenum 26 only when a known amount of drained liquid is accumulated. When the known amount of drained liquid is exceeded, the excess flows into the drain hole 28 and is discharged outside of the sanitizing device 15. Some drained liquid contained within the plenum 26 may also be dissipated by evaporation before, after, or during the operation of the sanitizing device. One or more thermistors 44 are mounted to the inside surface of the plenum 26. The thermistors 44 send temperature data to one or more of the electrical circuits 38 thus allowing temperature modulation within the sanitizing chamber 80 to occur.

The base 20 further supports a switch 36 used to control the operation of the sanitizing device 15. The switch 36 may be triggered manually. The switch 36 may be triggered to begin a preheat cycle of the sanitizing process or terminate any cycle of the sanitizing process while it is in progress. For safety purposes, any time the sanitizing cycle or preheat cycle are terminated by triggering switch 36, the cool down cycle automatically begins. One of the electrical circuits 38 automatically begins the cool down cycle in this situation.

The base 20 supports one or more electrical circuits 38. One of the electrical circuits 38 is an electrical timing circuit which tracks real time. The electrical timing circuit may control the heating element 40 and fan 42. The electrical timing circuit 38 may also send signals to other electrical circuits. Another electrical circuit 38 is a temperature control circuit. By cycling the heater element 40 and/or the fan 42, the temperature control circuit may keep the measured temperature within the sanitizing chamber 80 within the desired temperature range. Another of the electrical circuits 38 is an electrical error circuit. The electrical error circuit senses undesired operating conditions and may turn off the heating element 40, motor 23, and/or send an output signal to a light emitting diode 30 when such an operating condition exists. The electrical error circuit receives a signal from the electrical timing circuit and from one or more thermistors 44. These signals may be compared. Undesired operating conditions include when the sanitizing chamber 80 does not reach a desired temperature within a desired time or when the sanitizing chamber 80 reaches a desired temperature before a desired time elapses. When the temperature within the sanitizing chamber 80 does not reach a desired level within a desired time, typically either the heating element 40 or the motor 23 has malfunctioned or the cover 82 has not been placed securely upon the sanitizing device 15. When the temperature within the sanitizing chamber 80 reaches a desired level before a desired time, typically the sanitizing chamber 80 has been loaded with too many products thus, blocking airflow to the vents 83. Another undesired operating condition is excessive temperature within the sanitizing chamber 80 before the sanitizing process begins. An electrical circuit will not allow the sanitizing process to begin when this condition exists.

Figure 2:
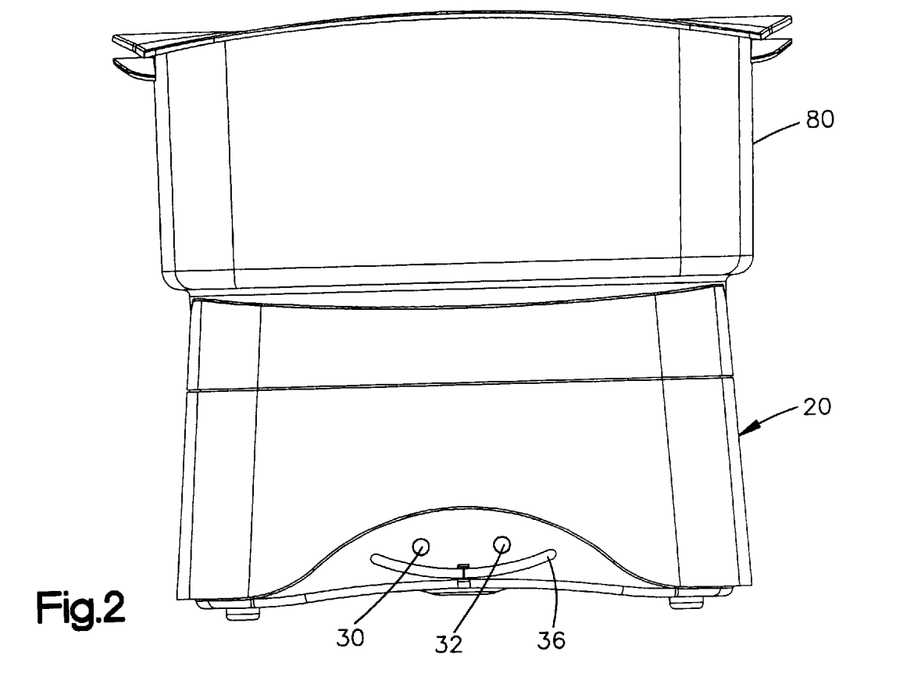
FIG. 2 is a front view of the sanitizer.

As shown in FIG. 2, the base 20 includes one or more light emitting diodes (LEDs) 30, 32. The LEDs 30, 32 are used to display one or more of the following operating conditions: preheat cycle in process, sanitizing cycle in process, cool-down cycle in process, and error conditions. The LEDs 30, 32 are controlled by signals from the electrical circuits 38.

Figure 7:
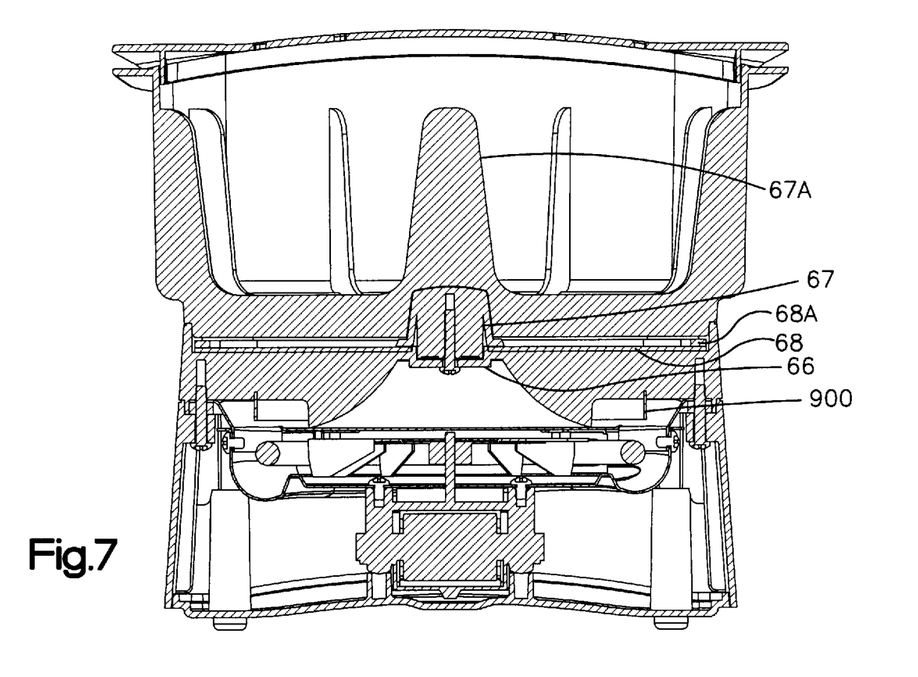
FIG. 7 is a cutaway view of the sanitizer.
Figure 8:
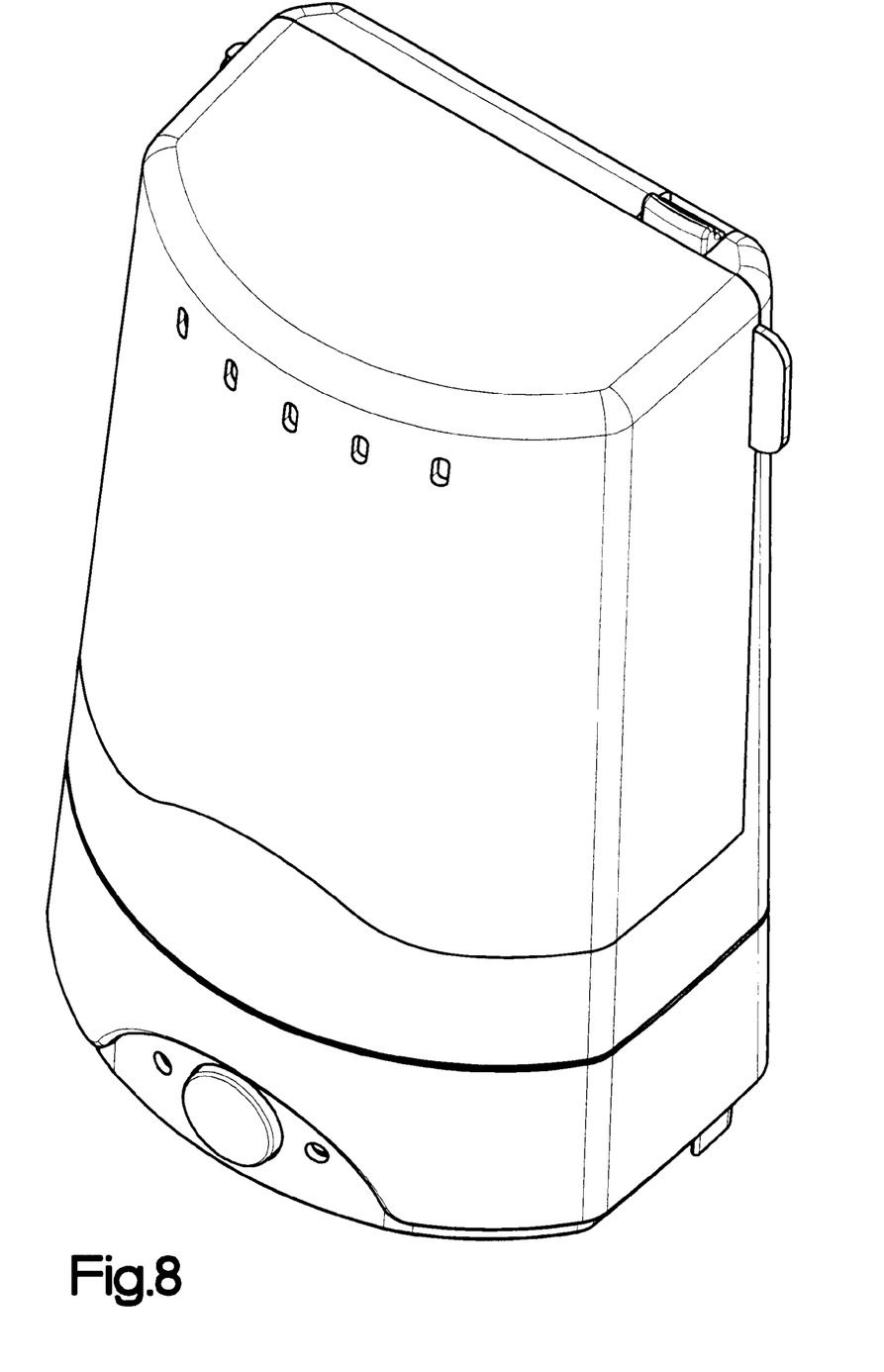
FIG. 8 is a perspective view of an alternate embodiment of the sanitizer.
Figure 9:
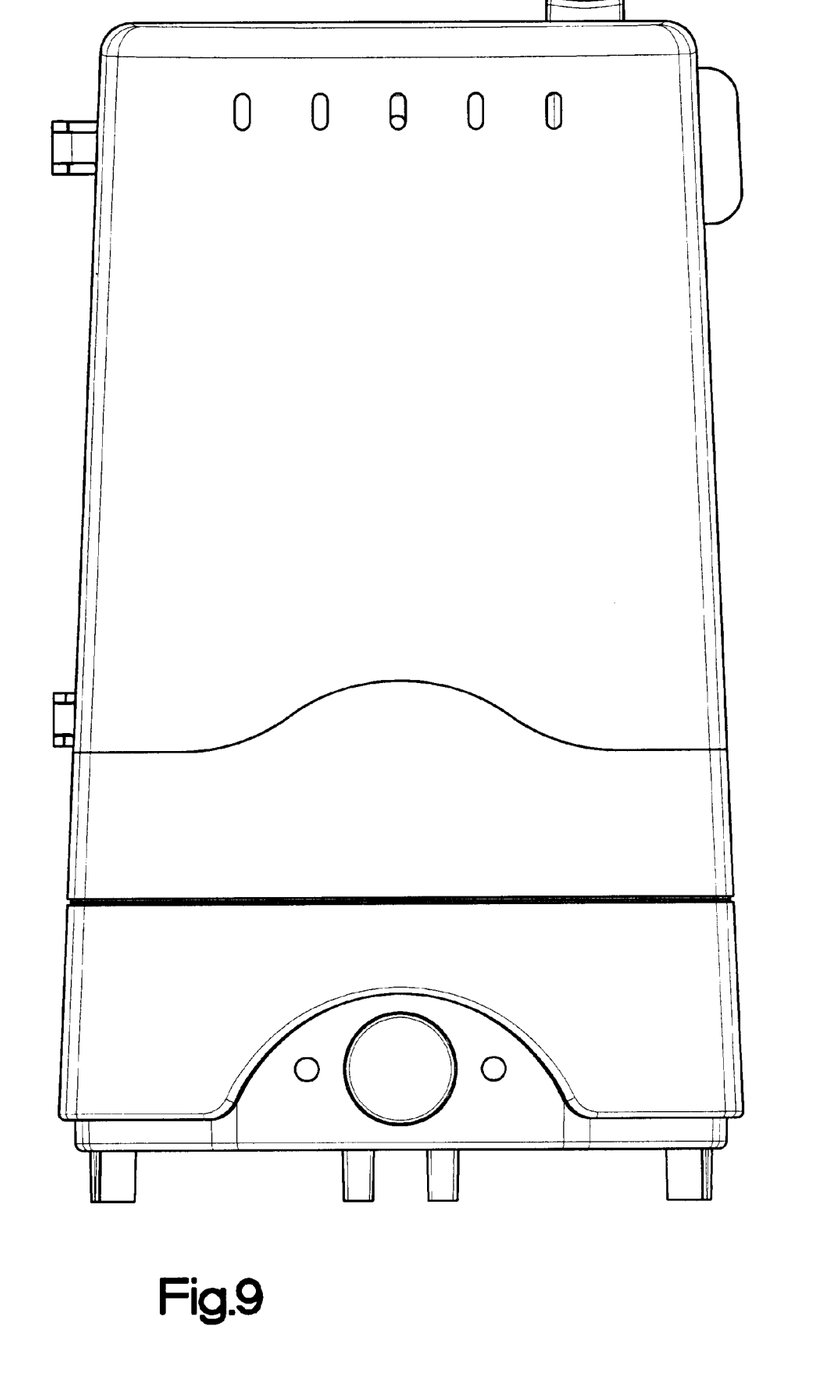
FIG. 9 is a front view of an alternate embodiment of the sanitizer.
Figure 10:
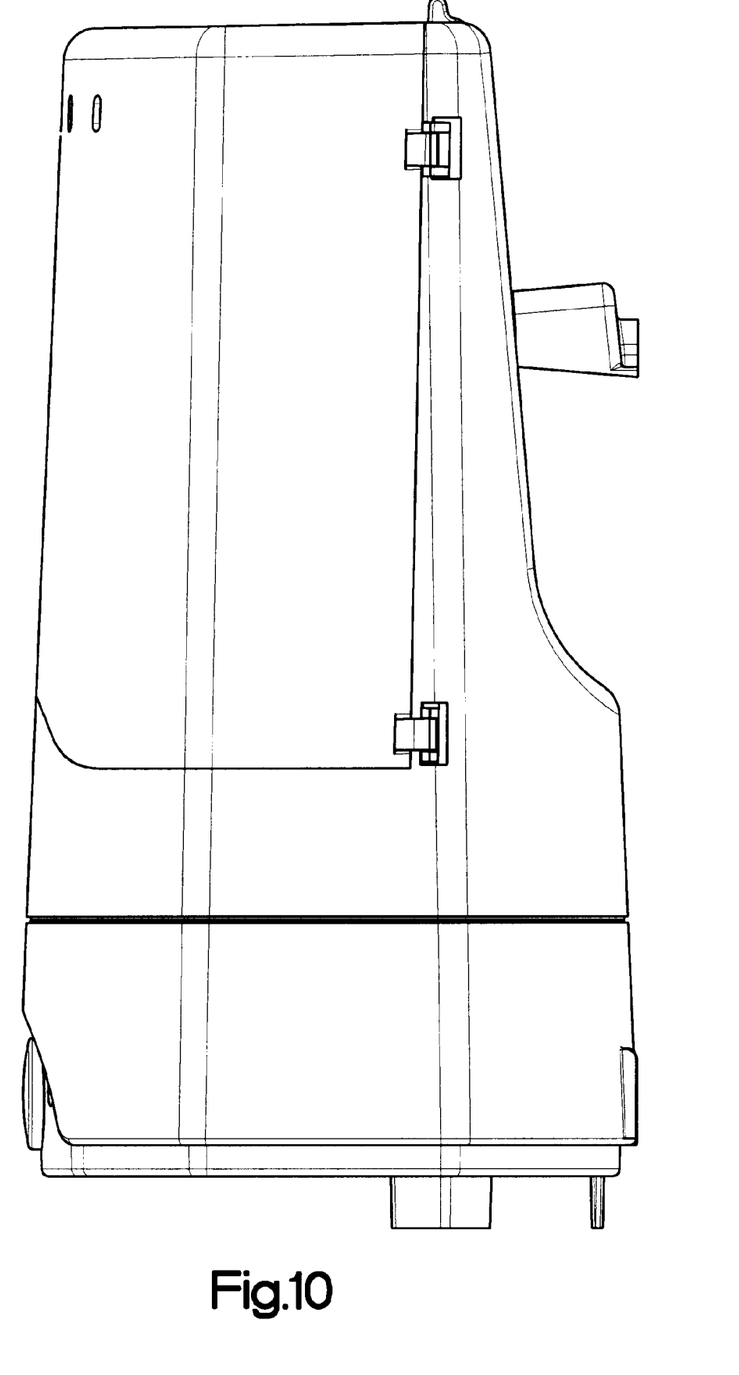
FIG. 10 is a side view of an alternate embodiment of the sanitizer.
Figure 11:
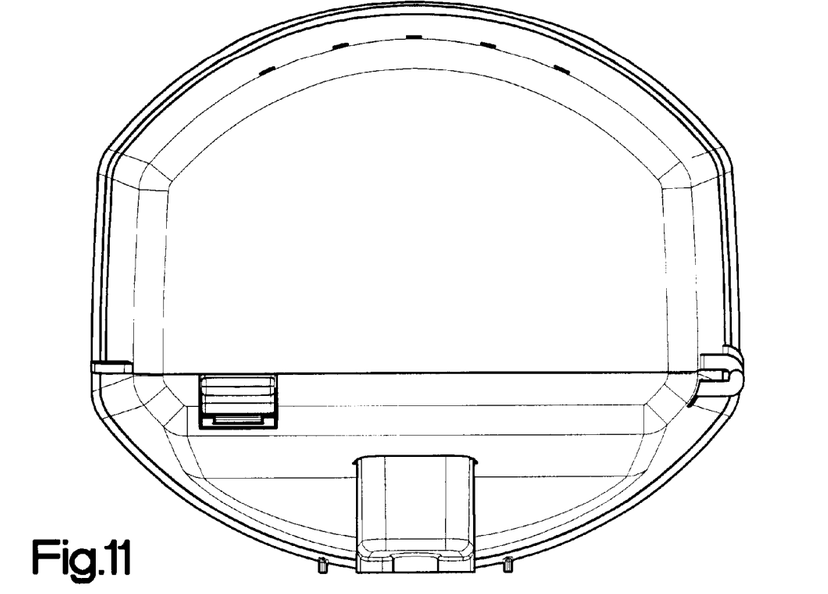
FIG. 11 is a top view of an alternate embodiment of the sanitizer.
Figure 12:
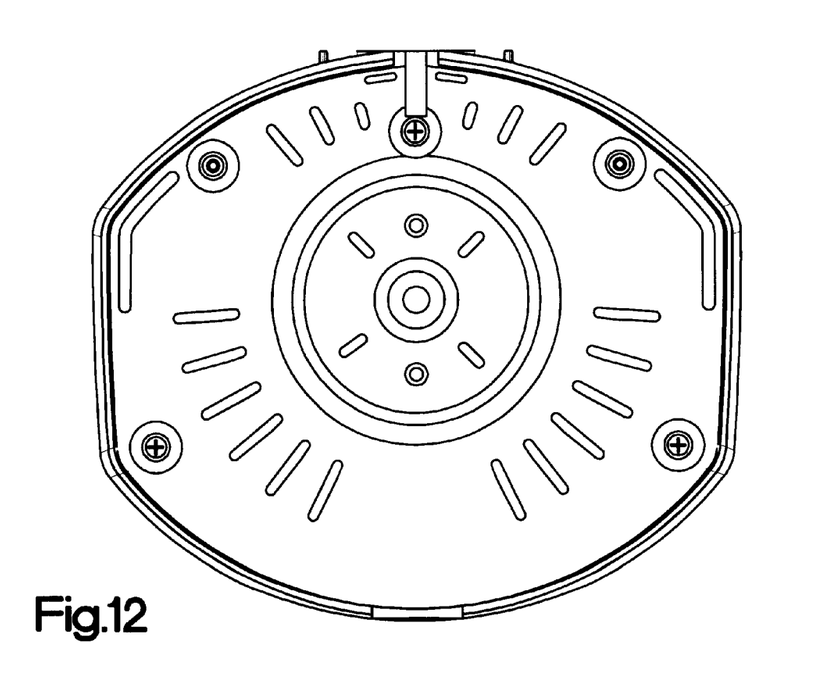
FIG. 12 is a bottom view of an alternate embodiment of the sanitizer.
Figure 13:
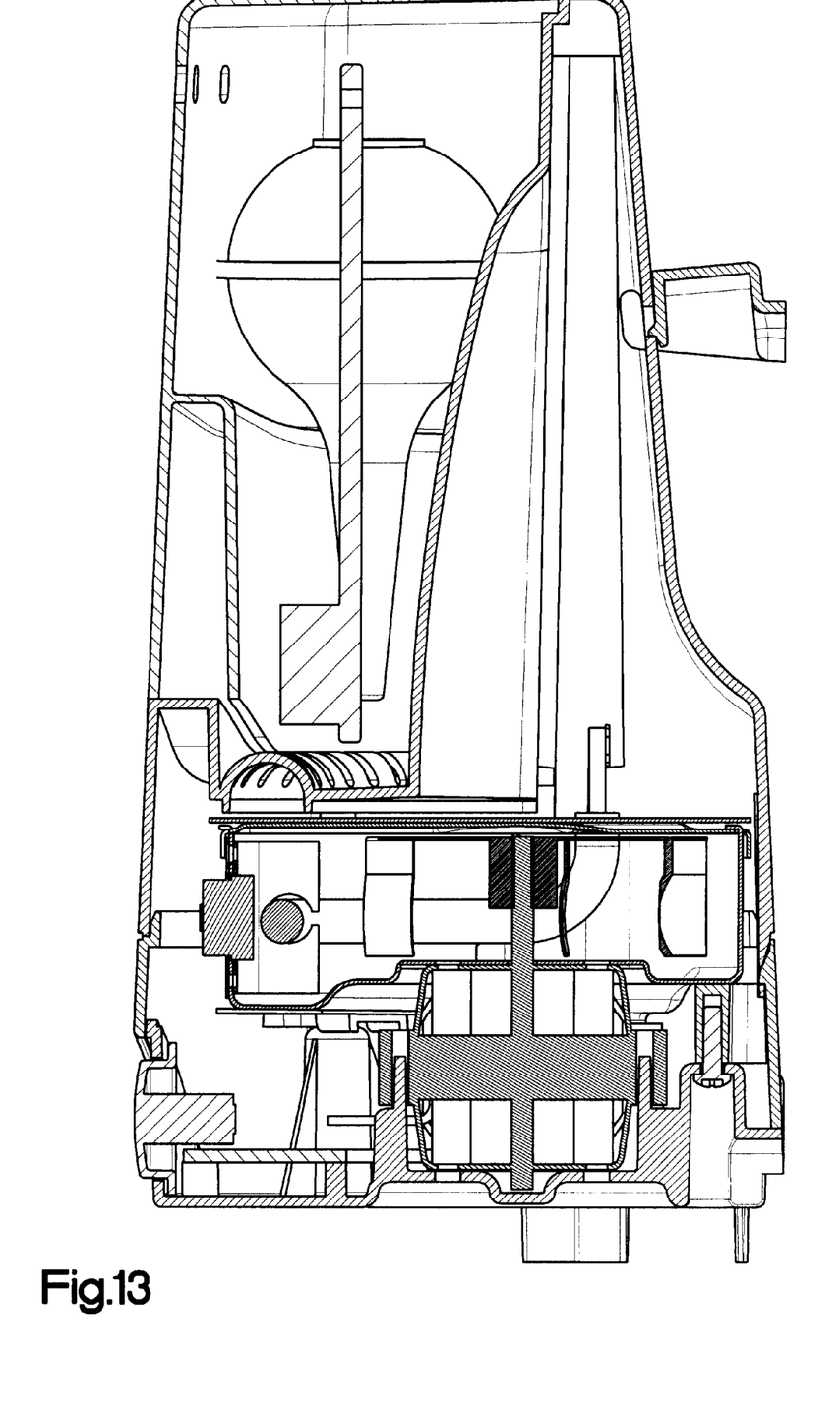
FIG. 13 is a cutaway view of an alternate embodiment of the sanitizer.

Referring back to FIG. 1, the sanitizing chamber 80 is located above the base 20. In between the sanitizing chamber 80 and the base 20 are a plenum cover 63, a manifold housing 64 and a screen 68. The plenum cover 63 is attached to the plenum 26 and the manifold housing 64. The plenum cover 63 acts as a junction between the rectangular manifold housing 64 and the bowl shaped plenum 26. The plenum cover 63 has a top and a bottom. The manifold housing 64 has a rectangular outer frame. Protruding from the interior of the outer frame are radial walls 65 which converge upon a central hub 66. Extending vertically from the central hub 66 is a central pillar 67 as shown in FIG. 7. A circumferential wall 900 protrudes from the bottom of the manifold housing 64. Referencing FIGS. 1 and 7, the manifold housing 64 helps distribute air evenly throughout the sanitizing chamber 80. The circumferential wall 900 radially divides air flow into inner and outer annular segments. The radial walls 65 divide airflow into circumferential segments. The manifold housing 64 supports a screen 68 and a screen retainer 68A. The screen 68 is rectangular and has a surface area equal to the surface area of the top of the manifold housing 64. The screen 68 has about 60% of its surface area open. The screen 68 prevents small household products from falling into the base 20 of the sanitizing device 15 from the sanitizing chamber 80 and prevents operator access to hot surfaces. The central pillar 67 may pass through a hole included in the center of the screen 68. In the illustration of FIG. 7, the central pillar 67 passes through the screen 68 into engagement with the central hub 66.

As shown in FIG. 1 the sanitizing chamber 80 is enclosed on its bottom by integral radiating ribs 901, which, as further illustrated in FIG. 7, may be extensions of the spacers 84, on its sides by a rectangular housing 81 and on its top by the cover 82. The rectangular housing 81 includes four sides which enclose the sanitizing chamber 80. The rectangular housing 81 is preferably made from a transparent, high temperature thermoplastic. Protruding from the four sides are a plurality of spacers 84. The spacers 84 are integrally formed with the side walls. As shown in FIG. 7, the ribs 901 are joined and a central rib 67A extends upwardly therefrom, above the central pillar 67. The spacers 84 prevent household products placed within the sanitizing chamber 80 from contacting the sides of the rectangular housing 81. Thus, heated air entering the sanitizing chamber 80 may contact all sides of the products to be sanitized. The central pillar 67 and central rib 67A, seen in FIG. 7, provide[s] the same benefit of allowing improved air flow around the household products. For optimal air flow, the spacers 84 are aligned vertically within the sanitizing chamber 80, however any spacer orientation may be used. Two of the four sides of the rectangular housing 81 are equipped with handles 86. The handles 86 may be used to remove the rectangular housing in the event of disassembly of the sanitizing device 15. The rectangular housing 81 may be cleaned using soap and water. Alternatively the handles 86 may be used as stationary anchors when the cover 82 is removed from the sanitizing device 15.

Figure 6:
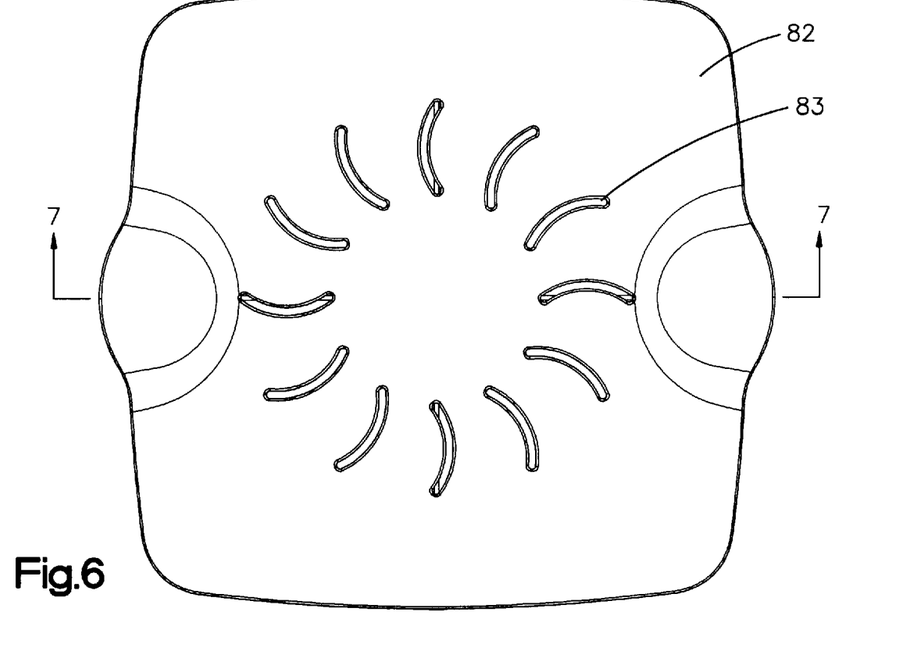
FIG. 6 is a top view of the sanitizer.

As shown in FIG. 6, a cover 82 encloses the top of the sanitizing chamber 80. The cover 82 is an arched rectangular plate having a group of vents 83. The vents 83 are juxtaposed arcuate slots and are arranged in the form of a circle. A portion of the heated air entering the sanitizing chamber 80 may leave the sanitizing chamber 80 through the vents 83. Thus, an ideal mass airflow rate through the sanitizing chamber 80 is established whereby a desirable thermal profile is maintainable in both the sanitizing cycle and the cool down cycle. The products within the sanitizing chamber 80 will also cool quickly after the sanitizing process is completed. Utilizing a small amount of force the cover 82 may be lifted out of position. The cover 82 is preferably made from transparent, high temperature thermoplastic.

FIGS. 8–13 show an alternate embodiment of the invention which may also be used to accommodate different sizes, shapes and orientations of items such as elongate bathroom products (syringes, toothbrushes, tweezers, combs) or any other bathroom or kitchen products requiring sanitization.

Products are sterilized by being placed within the sanitizing device 15 and being enveloped by hot air for a set period of time as described in more detail below.

Before the method is started the sanitizing device 15 must be assembled and placed upon a flat surface. The sanitizing device 15 must also have its power cord 100 inserted into a wall outlet. The first step of the sterilizing method is rinsing the household products to be sanitized. All products which are not made of cloth should be rinsed with tap water. Cloth products should be wiped clean with a damp cloth. After removing the cover 82, the household products are placed within the sanitizing chamber 80 of the sanitizing device 15. The cover 82 is then replaced.

The preheat cycle is starting by manual actuation of the switch 36. The preheat cycle occurs before the sanitizing cycle. During the preheat cycle the heating element 40 is increasing in temperature. The air temperature within the sanitizing chamber 80 during the preheat cycle is in a range from ambient room temperature (typically about 78 degrees Fahrenheit) to 149 degrees Fahrenheit. The preheat cycle has a duration of approximately 2 minutes. During the preheat cycle the motor 23 is running and the fan 42 is rotating. Thus, heated air is contacting the household products.

The preheat cycle is followed by the sanitizing cycle. During the sanitizing cycle, bacteria upon the household products may be destroyed. The air temperature within the sanitizing chamber 80 during the sanitizing cycle is in a range from 149 degrees Fahrenheit to 210 degrees Fahrenheit. The sanitizing cycle has a duration of approximately 11 minutes. During the sanitizing cycle the motor 23 is running and the fan 42 is rotating and the heating element 40 is being modulated by an electrical circuit. Thus, heated air is contacting the household products.

The sanitizing cycle is followed by a cooling cycle. During the cooling cycle, the heating element 40 is not energized. Temperature within the sanitizing chamber 80 falls from approximately 210 degrees Fahrenheit to ambient room temperature. The cooling cycle has a duration in a range from 6 to 8 minutes.

Operation of the sanitizing devices may be displayed by lighting an LED 30. Errors in the operation of the sanitizing device may also be displayed by lighting an LED 30. In one embodiment a single LED 30 is used. The single LED 30 is constantly illuminated during the preheat cycle and the sanitizing cycle. The single LED 32 remains on during the cool down cycle. The single LED 30 goes off at the end of the cooling cycle. The single LED 30 blinks if the temperature within the sanitizing chamber 80 reaches 149 degrees Fahrenheit too quickly. The single LED 30 also blinks if the temperature within the sanitizing chamber 80 does not reach 149 degrees Fahrenheit fast enough. In another embodiment, a first LED 30 and second LED 32 are used. The first LED 30 is constantly illuminated during the preheat cycle and the sanitizing cycle, while the second LED 32 is off. The second LED 32 is constantly illuminated during the cooling cycle, while the first LED 32 is off. The second LED 32 goes off at the end of the cooling cycle. The first LED 30 blinks if the temperature within the sanitizing chamber 80 reaches 149 degrees Fahrenheit too quickly. The first LED 30 also blinks if the temperature within the sanitizing chamber does not reach 149 degrees Fahrenheit fast enough.

This superior sanitizer can destroy bacteria on plastic and cloth household products. Because of a superior spacer system, products do not need to be specially arranged to guarantee full sanitization. A novel ventilation system keeps the sanitizing chamber at a desired temperature and allows the products to cool down quickly after being sanitized. An LED display is able to show when the sanitizer is functioning and also when the sanitizer has overheated or is not warm enough. Although the device and method have been shown and described with reference to certain embodiments, minor variations and insubstantial differences in the various combination of materials and methods of application may occur to those of ordinary skill in the art while remaining within the scope of the invention as claimed and equivalents.

We claim:

1. A sanitizing device for household products comprising
   (a) a heating element;
   (b) a sanitizing chamber having a sidewall and a central portion;
   (c) spacers integrally formed with and extending vertically from and toward said central portion of said sanitizing chamber side wall;
   (d) a fan which moves air across said heating element and into said sanitizing chamber; and
   (e) one or more vents which allow said air to exit said sanitizing chamber.

2. The sanitizing device of claim 1 wherein said sanitizing chamber comprises a rectangular housing and a cover.

3. The sanitizing device of claim 2 wherein said sanitizing chamber is manufactured from a transparent, high temperature thermoplastic.

4. The sanitizing device of claim 1 wherein said spacers are oriented vertically.

5. The sanitizing device of claim 1 wherein said vents are within a cover.

6. The sanitizing device of claim 5 wherein said vents of said cover are a group of arcuate slots arranged in a circle.

7. The sanitizing device of claim 1 further including a bowl-shaped plenum located beneath said heater element and said sanitizing chamber, said plenum having a sloped plenum base able to catch excess moisture from said sanitizing chamber and said bowl-shaped plenum further having a drain hole to drain said excess moisture from said sanitizing device.

8. The sanitizing device of claim 1 further including an electrical timing circuit.

9. The sanitizing device of claim 1 further including a electrical error circuit.

10. The sanitizing device of claim 1 further including an LED display.

11. The sanitizing device of claim 1 wherein said sanitizing chamber sidewall has a predetermined height and said spacers extend vertically at least two-thirds of said height.

12. The sanitizing device of claim 1 wherein said sanitizing chamber includes an open bottom provided with spaced ribs.

13. The sanitizing device of claim 12 wherein said sanitizing chamber ribs are integral with said spacers and are joined at a central portion of said sanitizing chamber.

14. The sanitizing device of claim 12 further including a central rib extending from said central portion of said sanitizing chamber.

15. The sanitizing device of claim 1 further including a screen below said sanitizing chamber.

16. A sanitizing device for household products comprising
 (a) a heating element;
 (b) a sanitizing chamber;
 (c) spacers integrally formed with and protruding from said sanitizing chamber;
 (d) a fan which moves air across said heating element and into said sanitizing chamber;
 (e) at least one vent which allows air to exit said sanitizing chamber; and
 (f) a manifold housing located above said heating element and below said sanitizing chamber, said manifold housing including an outside frame and a central pillar and spokes extending from said outside frame to said central pillar.

* * * * *